(12) United States Patent
Beller et al.

(10) Patent No.: US 7,081,544 B2
(45) Date of Patent: Jul. 25, 2006

(54) CHIRAL LIGANDS, TRANSITION METAL COMPLEXES THEREOF, AND THE CATALYTIC USE OF THE SAME

(75) Inventors: Matthias Beller, Nienhagen (DE); Kathrin Junge, Rostock (DE); Axel Monsees, Frankfurt (DE); Thomas Riermeier, Floersheim (DE); Harald Trauthwein, Munich (DE)

(73) Assignee: Degussa AG, Duesseldorf (DE)

( * ) Notice: Subject to any disclaimer, the term of this patent is extended or adjusted under 35 U.S.C. 154(b) by 50 days.

(21) Appl. No.: 10/491,953

(22) PCT Filed: Jun. 18, 2002

(86) PCT No.: PCT/EP02/06715

§ 371 (c)(1),
(2), (4) Date: Apr. 8, 2004

(87) PCT Pub. No.: WO03/033510

PCT Pub. Date: Apr. 24, 2003

(65) Prior Publication Data

US 2004/0249184 A1 Dec. 9, 2004

(30) Foreign Application Priority Data

Oct. 15, 2001 (DE) ................. 101 50 335

(51) Int. Cl.
*C07F 9/22* (2006.01)
*C07F 9/28* (2006.01)

(52) U.S. Cl. ............................ 558/385; 562/9; 564/16; 568/12

(58) Field of Classification Search ................ 558/385; 562/9; 564/16; 568/12
See application file for complete search history.

(56) References Cited

FOREIGN PATENT DOCUMENTS

EP 0686639 12/1995
WO WO 01/14299 A1 * 3/2001

OTHER PUBLICATIONS

Bitterer et al., PH-Functional Phosphines with 1,1'-Biphenyl-2,2'-bis(methylene) and 1,1'-Binaphthyl-2-2'-bis(methylene) Backbones, Inorg. Chem.; (Article); 1998; 37(25); 6408-6417.*
Gladiali et al., Novel Atropisomeric Phosphorus Ligands: 4,5-Dihydro-3H-dinaphtho[2,1-c;1',2'-e] Phosphepine Derivatves, Tetrahedron Asymmetry, 1994, 5 (4) 511-514.*
Vedejs, E. et al: "Enantioselective Acylations Catalyzed by Chiral Phosphines" J. Org. Chem. (1996), 61(2), 430-1, XP002208471.
Gladiali, Serafino et al: "Novel atropisomeric phosphorus ligands: 4, 5-dihydro-3H-dinaphtho '2, 1-c; 1', 2'-elphosphepine derivatives" Tetrahedron: Asymmetry (1994), 5(4), 511-14, XP001093902 p. 512.
Stranne, Robert et al: "Synthesis and application of chiral P, N-ligands with pseudo-meso and pseudo-C2 symmetry" Organic Letters (2001), 3(16), 2525-2528, XP002208472.
Bitterer, Frank et al: "PH-Functional Phosphines with 1,1'-Biphenyl-2,2'-bis(methylene) and 1,1'-Binaphthyl-2,2'-bis(methylene) Backbones" Inorganic Chemistry (1998), 37(25), 6408-6417, XP002208473.
Soulier, Eric et al: "Phosphane and bis(phosphane) ligands from phosphinic acids" European Journal of Organic Chemistry (2000), (20), 3497-3503, XP002208474.
Soulier, Eric et al: "A convenient access to new phosphine and diphosphine ligands form phosphinic acids" Tetrahedron Letters (1998), 39(24), 4291-4294, XP002208475.

* cited by examiner

*Primary Examiner*—Johann Richter
*Assistant Examiner*—Chukwuma Nwaonicha
(74) *Attorney, Agent, or Firm*—Oblon, Spivak, McClelland, Maier & Neustadt, P.C.

(57) ABSTRACT

The invention relates to novel chiral ligands of formula (I), the production thereof and the use of the same in catalytic reactions.

24 Claims, No Drawings

CHIRAL LIGANDS, TRANSITION METAL COMPLEXES THEREOF, AND THE CATALYTIC USE OF THE SAME

The present invention concerns novel chiral phosphane ligands and their use in catalytic reactions.

Chiral organophosphorus compounds as ligands in homogeneous catalysis have steadily grown in importance over recent years. Chiral phosphane ligands in particular are used in industry as components of catalysts for the production of fine chemicals or of intermediates for pharmaceuticals and agrochemicals. Moreover, such catalytic methods and industrial processes are continually being developed further with the aim of improving novel catalyst and ligand systems.

The suitability of certain phosphorus-containing ligands for the catalytic reaction of specific substrates depends on the steric and electronic properties at the coordinating phosphorus atom. By varying the substituents at the phosphorus in such compounds, the electronic and steric properties of the phosphorus ligand can be directly influenced such that selectivity and activity in homogeneous catalytic processes can be controlled.

Enantiomer-concentrated chiral-ligands are used in asymmetrical synthesis or asymmetrical catalysis, it being of substantial importance that the electronic and the stereochemical properties of the ligand be optimally adjusted to the individual catalysis problem. There is thus a great need for chiral ligands exhibiting stereochemical and electronic differences in order to find the ideal "tailor-made" ligand for a particular asymmetrical catalysis.

Chiral ligands are used for example in stereoselective hydrogenation reactions of olefins, for example for the production of enantiopure amino acid derivatives. A general article describing this method can be found for example in M. Beller, C. Bolm, Transition Metals for Organic Synthesis, Vol. 2, p. 13, VCH-Wiley, Weinheim 1998. Other commonly used methods for synthesising chiral compounds using chiral phosphane ligands are e.g. asymmetrical allyl substitutions, asymmetrical coupling reactions (Heck reaction, Suzuki reaction, Negishi coupling) and asymmetrical cyanations and vinylations.

Chelating phosphane ligands are used in all these reactions in order to obtain high enantioselectivities. The preparation of chelating ligands is often more difficult than the production of simpler, monodentate phosphane ligands. There is therefore a great deal of interest in novel monodentate phosphane ligands that allow highly enantioselective reactions.

The fact that monodentate chiral phosphorus-containing ligands are also suitable as chiral ligands for performing enantioselective catalytic processes is described in a general article by I. V. Komarev, A. Börner, Angew. Chem. 2001, 113, 1237 by reference to phosphite and aminophosphonite ligands. However, the ligands described there are unsuitable for many catalytic reactions that can be performed with the aid of phosphane ligands.

There is therefore a great need for novel, monodentate chiral phosphane ligands that are easy to produce and that allow an enantioselective reaction course.

This object is achieved by ligands having the general formula I

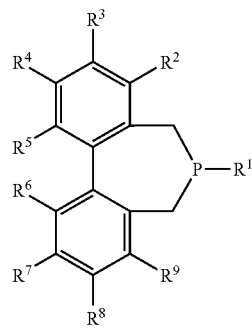

(I)

wherein in formula I $R^1$ represents a hydrogen, alkyl, alkenyl, aromatic or heteroaromatic aryl, O-alkyl, NH-alkyl, N-(alkyl)$_2$, wherein the two alkyl radicals can also be linked together directly or via an oxygen bridge, O-(aryl), NH-(aryl), N-(alkyl)(aryl) radical, $R^2$ to $R^9$ mutually independently have the meaning of $R^1$ or stand for a radical selected from the group comprising O—CO-alkyl, O—CO-aryl, F, Cl, Br, OH, NO$_2$, Si(alkyl)$_3$, CF$_3$, CN, CO$_2$H, COH, SO$_3$H, CONH$_2$, CONH(alkyl), CON(alkyl)$_2$, SO$_2$(alkyl), SO(alkyl), SO(aryl), SO$_2$(aryl), SO$_3$(alkyl), SO$_3$(aryl), S-alkyl, S-aryl, NH—CO(alkyl), CO$_2$(alkyl), CONH$_2$, CO(alkyl), NHCOH, NHCO$_2$(alkyl), CO(aryl), CO$_2$(aryl), CH=CH—CO$_2$(alkyl), CH=CH—CO$_2$H, PO(aryl)$_2$, PO(alkyl)$_2$, PO$_3$H, PO(O-alkyl)$_2$, wherein in each case two or more adjacent radicals can mutually independently also be linked together to form a condensed ring system, and wherein in $R^1$ to $R^9$ alkyl stands for a hydrocarbon radical with 1 to 12 C atoms and alkenyl for a monounsaturated or polyunsaturated hydrocarbon radical with 2 to 4 C atoms, each of which can be linear or branched and can be substituted with Cl, F, alkyl (C$_{1-C12}$), O-alkyl (C$_{1-C12}$), (C$_{5-C10}$) aryl, O—(C$_{5-C10}$) aryl, NH$_2$, NH(alkyl (C$_{1-C12}$)), N(alkyl (C$_{1-C12}$))$_2$, and aryl stands for a five- to ten-membered aromatic radical, which can be substituted with Cl, F, Br, alkyl (C$_{1-C12}$), O-alkyl (C$_{1-C12}$), (C$_{5-C10}$) aryl, O—(C$_{5-C10}$) aryl, NH$_2$, NH(alkyl (C$_1$–C$_{12}$)), N(alkyl (C$_{1-C12}$))$_2$, wherein one to four carbon atoms in the aromatic radical can also be replaced by heteroatoms from the group comprising nitrogen, oxygen and sulfur to form a five- to ten-membered heteroaromatic radical.

For $R^1$ radicals from the group comprising alkyl, aryl or heteroaryl, O-alkyl, NH-alkyl, N-(alkyl)$_2$, piperidine, morpholine, O-(aryl), NH-(aryl), N-(alkyl)(aryl) are preferred. Preferred radicals $R^2$ to $R^9$ are mutually independently selected from the group comprising O—CO-alkyl, O—CO-aryl, Br, CONH$_2$, CONH(alkyl), CON(alkyl)$_2$, SO(alkyl), SO(aryl), SO$_2$(alkyl), SO$_2$(aryl), SO$_3$(alkyl), SO$_3$(aryl), NH—CO(alkyl), CO$_2$(alkyl), CONH$_2$, CO(alkyl), NHCOH, NHCO$_2$(alkyl), CO$_2$(aryl), PO(alkyl)$_2$, PO(O-alkyl)$_2$ radicals; the radicals are particularly preferably hydrogen, alkyl, aryl or heteroaryl, O-alkyl, NH-alkyl, N-(alkyl)$_2$, O-(aryl), NH-(aryl), N-(alkyl)(aryl), F, Cl, OH, CO$_2$H, SO$_3$H, CO(alkyl), CO(aryl), PO(aryl)$_2$, PO$_3$H.

In $R^1$ to $R^9$ alkyl and alkenyl preferably stand for a hydrocarbon radical with 1 to 4 C atoms, the alkenyl group possessing a double bond, and aryl for a five- to seven-membered aromatic radical. Heteroaromatic aryl radicals preferably contain one or two nitrogen atoms, one nitrogen and one oxygen atom or one sulfur or one oxygen atom.

Formula I also encompasses ligands containing condensed ring systems, wherein two or more adjacent radicals $R^2$ to $R^9$ are linked together. In preferred condensed ring systems the linked radicals form cycloaliphatic and aromatic rings, particularly preferably five- to seven-membered cycloaliphatic and six-membered aromatic ring systems. The linkage preferably occurs via a direct single or double bond or via a $(C_1–C_3)$ alkyl or alkenyl group with one or two double bonds.

Particularly preferred ligands having the formula I accordingly have a substitution pattern wherein $R^1$ represents an alkyl, aryl or heteroaryl radical, O-alkyl, NH-alkyl, $N(alkyl)_2$, O-(aryl), NH-(aryl), N-(alkyl)(aryl),
$R^2$ to $R^9$ mutually independently have the meaning of $R^1$ or also represent a radical from the group comprising hydrogen, F, Cl, OH, $CO_2H$, $SO_3H$, CO(alkyl), CO(aryl), $PO(aryl)_2$, $PO_3H$, wherein in each case two or more adjacent radicals can mutually independently also be linked together to form a condensed ring system, and wherein the alkyl, alkenyl, aromatic or heteroaromatic aryl groups have the above definition and can carry the aforementioned substituents.

For the synthesis of the ligands according to the invention the use of enantiopure dimethyl compounds having the formula II with subsequent lithiation with alkyl lithium compounds, followed by reaction with aminophosphorus dichlorides or alkyl or aryl phosphorus dichlorides, has proven particularly effective.

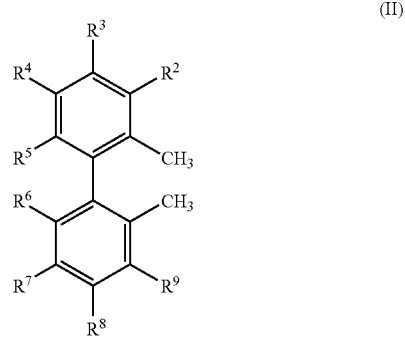

(II)

A large number of the ligands according to the invention can advantageously be prepared from the corresponding 4-chlorophosphepine, which can be obtained by $HCl/Et_2N$ exchange from the respective 4-aminophosphepine, by reaction with amines, alcohols and Grignard reagents.

Compounds having the formula I can easily be produced using this process, wherein the desired substitution pattern at the ligand can be obtained by choosing suitable substituted educts. In addition, as described just above, the radical $R^1$ can also subsequently be modified or exchanged.

The ligands according to the invention having the formula I are used with transition metals as catalysts.

The production of metal-ligand co-ordination compounds can take place in situ by reacting a metal salt or a corresponding pre-complex with the ligands having the general formula (I). A metal-ligand co-ordination compound can also be obtained by reacting a metal salt or a corresponding pre-complex with the ligands having the general formula (I), with subsequent isolation. The production of such a co-ordination compound preferably takes place in a one-pot reaction with stirring at elevated temperature. Catalytically active co-ordination compounds can also be produced directly in the reaction batch for the planned catalytic reaction.

Examples of the metal salts are metal chlorides, bromides, iodides, cyanides, nitrates, acetates, acetylacetonates, hexafluoroacetylacetonates, tetrafluoroborates, perfluoroacetates or triflates, particularly of palladium, platinum, rhodium, ruthenium, osmium, iridium, cobalt, nickel or/and copper.

Suitable pre-complexes for the production of catalysts are, for example, cyclooctadiene palladium chloride, cyclooctadiene palladium iodide, 1,5-hexadiene palladium chloride, 1,5-hexadiene palladium iodide, bis(dibenzylidene acetone) palladium, bis(acetonitrile) palladium(II) chloride, bis(acetonitrile) palladium(II) bromide, bis(benzonitrile) palladium(II) chloride, bis(benzonitrile) palladium(II) bromide, bis(benzonitrile) palladium(II) iodide, bis(allyl) palladium, bis(methallyl) palladium, allyl palladium chloride dimer, methallyl palladium chloride dimer, tetramethyl ethylene diamine palladium dichloride, tetramethyl ethylene diamine palladium dibromide, tetramethyl ethylene diamine palladium diiodide, tetramethyl ethylene diamine palladium dimethyl, cyclooctadiene platinum chloride, cyclooctadiene platinum iodide, 1,5-hexadiene platinum chloride, 1,5-hexadiene platinum iodide, bis(cyclooctadiene) platinum, potassium (ethylene trichloroplatinate), cyclooctadiene rhodium(I) chloride dimer, norbornadiene rhodium(I) chloride dimer, 1,5-hexadiene rhodium(I) chloride dimer, tris(triphenyl phosphane) rhodium(I) chloride, hydridocarbonyl tris(triphenyl phosphane) rhodium(I) chloride, bis(cyclooctadiene) rhodium(I) perchlorate, bis(cyclooctadiene) rhodium(I) tetrafluoroborate, bis(cyclooctadiene) rhodium(I) triflate, bis(acetonitrile cyclooctadiene) rhodium(I) perchlorate, bis(acetonitrile cyclooctadiene) rhodium(I) tetrafluoroborate, bis(acetonitrile cyclooctadiene) rhodium(I) triflate, cyclopentadiene rhodium(III) chloride dimer, pentamethyl cyclopentadiene rhodium(III) chloride dimer, (cyclooctadiene) $Ru(\mu^3-allyl)_2$, ((cyclooctadiene) $Ru)_2$ (acetate)$_4$, ((cyclooctadiene)Ru)$_2$ (trifluoroacetate)$_4$, $RuCl_2$(arene) dimer, tris(triphenyl phosphane) ruthenium(II) chloride, cyclooctadiene ruthenium(II) chloride, $OsCl_2$(arene) dimer, cyclooctadiene iridium(I) chloride dimer, bis(cyclooctene) iridium (I) chloride dimer, bis(cyclooctadiene) nickel, (cyclododecatriene) nickel, tris(norbornene) nickel, nickel tetracarbonyl, nickel(II) acetylacetonate, (arene) copper triflate, (arene) copper perchlorate, (arene) copper trifluoroacetate, cobalt carbonyl.

The ligands according to the invention can be used in catalytic reactions as isolated complexes of the cited transition metals, but they can also be used in their in situ form.

Catalytic reactions in which the ligands according to the invention or complexes thereof are used are for example catalytic hydrogenations, hydrosilylations, aminations, allyl substitutions, Grignard couplings, Heck and Suzuki reactions, hydrocyanations, hydrovinylations, hydroformylations, hydroacylations and hydrocarboxylations.

Preferred reactions are catalytic hydrogenations, hydrosilylations, allyl substitutions, hydrocyanations, hydroformylations and hydrocarboxylations.

Catalytic hydrogenations are particularly preferred.

The catalytic reactions are preferably performed in solution, organic solvents such as e.g. ethyl acetate, THF, methanol, toluene, acetone, or $CH_2Cl_2$ having proven suitable. Furthermore, very high enantioselectivities can be achieved, e.g. in asymmetrical hydrogenation, by the addition of SDS (sodium dodecyl sulfate). Relative to the substrate used, the addition of SDS in a molar ratio of 1:0.01 to 1:2, preferably between 1:0.1 and 1:0.5, has proven effective. In asymmetrical hydrogenation in toluene in particular, a previously unattained enantioselectivity in the reaction was acheieved by the addition of SDS in the molar ratio of 1:0.2.

With the ligands according to the invention high catalyst turnover values in the order of 1000 or more can be achieved in combination with high enantioselectivities. With the ligands according to the invention it is thus possible to perform reactions with small amounts of catalyst, in other words with high catalyst productivity, thereby minimising catalyst costs. The ligands according to the invention are also simple to produce. In addition to the good catalytic properties, a large number of differently substituted ligands can easily be obtained by choosing suitable educts for the ligand synthesis. This opens up the possibility of selecting ligands having the formula I which are optimised in terms of their electronic and steric properties for a specific synthesis. For these reasons the ligands described can be used in industry for a large number of catalytic syntheses.

EMBODIMENT EXAMPLES

General work instructions for the synthesis of ligands according to the invention Method 1:

29.4 ml of a 1.6 m n-BuLi solution in hexane (0.047 mol n-BuLi) are introduced into a 250 ml three-necked flask and freed from solvent in vacuo. The yellow, oily residue is taken up in 15 ml diethyl ether and cooled down to 0° C. 0.019 mol 2,2'-dimethyl-1,1'-diphenyl derivative dissolved in 20 ml diethyl ether are then added in portions. The red coloration becomes more intensive after the addition of 7 ml (0.047 mol) TMEDA. The blood-red reaction solution is heated to room temperature. After 2–48 h crystals precipitate out. The supernatant solution is decanted and the crystal paste washed with a little pentane. Drying in vacuo yields 50–85% regioselective dilithiated 2,2'-dimethyl-1,1'-diphenyl derivative.

The dilithium salt of the 2,2'-dimethyl-1,1'-diphenyl derivative is suspended in 35 ml hexane at 0° C. 1.1 eq. of the respective dichlorophosphine $Cl_2PR^1$ ($R^1$=Et, t-Bu, Ph, $NEt_2$, $NMe_2$) dissolved in 15 ml hexane are added in portions, giving rise to a discoloration. On completion of the addition the reaction mixture is heated to room temperature and refluxed for 2 h to complete the reaction. The solvent hexane is replaced by toluene. If $R^1$=alkyl or aryl the LiCl is separated off by hydrolysis with degasified water. The phosphane ligands can be isolated from the dried organic phase by crystallisation. If $R^1$=N-alkyl$_2$, N-aryl$_2$, NH-alkyl, NH-aryl, O-alkyl, O-aryl, LiCl is separated off in a closed sintered-glass filter. The phosphorus amidites can be obtained by evaporating the solvent to low volume or by covering it with a layer of hexane.

Method 2:

0.026 mol of the corresponding phosphorus amidite $R_1$=$NEt_2$ (same representation as in method 1) are suspended in 300 ml cyclohexane in a 1 l three-necked flask. The apparatus is fitted with a gas-entry tube and cooled to 0° C. HCl gas is passed through the suspension for 1 h with vigorous stirring, during which time the precipitate dissolves. Excess HCl is stirred for a further hour under a light argon stream. The precipitate is then separated off through a sintered-glass filter and washed twice with 100 ml cyclohexane. The solvent is evaporated to one third of its volume and covered with a layer of hexane. 70–95% of the respective chlorophosphine can be isolated as a crystalline powder.

$7.9*10^{-3}$ mol of the chlorophosphine produced in this way are dissolved in 20 ml diethyl ether and 20 ml THF and 1.1 eq. RMgX (R=i—Pr, X=Cl) are added in portions at room temperature. On completion of the addition the mixture is refluxed for 2 h. It is then hydrolysed with 40 ml degasified water, the dried ethereal phase evaporated to low volume and taken up in 10 ml toluene. The ligand is isolated as a crystalline precipitate.

Examples of the ligands according to the invention that were produced by the methods described (examples 1) to 7)):

1) 4-Phenyl-4,5-dihydro-3H-dinaphtho[2,1-c; 1',2'-e]phosphepine: $^{31}$P-NMR ($C_6D_6$): 6.7 ppm; MS m/z: 388 [M+].
2) 4-t-Butyl-4,5-dihydro-3H-dinaphtho[2,1-c; 1',2'-e]phosphepine: $^{31}$P-NMR ($C_6D_6$): 29.6 ppm; MS m/z: 368 [M+], 311, 265.
3) 4-i-Propyl-4,5-dihydro-3H-dinaphtho[2,1-c; 1',2'-e]phosphepine: $^{31}$P-NMR ($C_6D_6$): 21.8 ppm; MS m/z: 354 [M+], 311, 265.
4) 4-Ethyl-4,5-di-hydro-3H-dinaphtho[2,1-c; 1',2'-e]phosphepine: $^{31}$P-NMR ($C_6D_6$): 8.5 ppm; MS m/z: 340 [M+].
5). 4-Diethylamino-4,5-dihydro-3H-dinaphto-[2,1-c; 1',2'-e]phosphepine: $^{31}$P-NMR ($C_6D_6$): 73.0 ppm; MS m/z: 383 [M+], 340, 313, 265.
6) 4-Dimethylamino-4,5-dihydro-3H-dinaphtho[2,1-c;1',2'-e]phosphepine: $^{31}$P-NMR ($C_6D_6$): 77.0 ppm; MS m/z: 355 [M+].
7) 4-Chloro-4,5-dihydro-3H-dinaphtho[2,1-c; 1',2'-e]phosphepine: $^{31}$P-NMR ($C_6D_6$): 115.1 ppm; MS m/z: 347 [M+1], 329, 311, 283.

The following additional compounds (examples 8) to 17)) were produced in the same way following the general work instructions:

8) 4-Methyl-4,5-dihydro-3H-dinaphtho[2,1-c; 1',2'-e]phosphepine,
9) 4-p-Methoxyphenyl-4,5-dihydro-3H-dinaphtho[2,1-c; 1',2'-e]-phosphepine
10) 4-p-Trifluoromethylphenyl-4,5-dihydro-3H-dinaphtho[2,1-c; $_1$',2'-e]phosphepine
11) 4-Methoxy-4,5-dihydro-3H-dinaphtho[2,1-c; 1',2'-e]phosphepine,
12) 4-Ethoxy-4,5-dihydro-3H-dinaphtho[2,1-c; 1',2'-e]phosphepine,
13) 4-Benzyloxy-4,5-dihydro-3H-dinaphtho[2,1-c; 1',2'-e]phosphepine,
14) 4-Di-1-propylamino-4,5-dihydro-3H-dinaphtho[2,1-c; 1',2'-e]phosphepine,
15) 4-Piperidyl-4,5-dihydro-3H-dinaphtho[2,1-c; 1',2'-e]phosphepine,
16) 6-Diethylamino-1,11-dimethoxy-6-phospha-dibenzo[a,c]cycloheptene,
17) 6-Dimethylamino-1,11-dimethoxy-6-phospha-dibenzo[a,c]cycloheptene,
18) 6-Methyl-1,11-dimethoxy-6-phospha-dibenzo[a,c]cycloheptene,
19) 6-Ethoxy-1,11-dimethoxy-6-phospha-dibenzo[a,c]cycloheptene.

General work instructions for catalytic hydrogenations:

Under an argon atmosphere 0.025 mmol [Rh(COD)$_2$]BF$_4$, 0.055 mmol ligand and 0.5 mmol (Z)-α-acetaminocinnamic acid methyl ester are added to 12.5 ml of the dried and degasified solvent in a hydrogenating vessel at a temperature of 25° C. and stirred for 15 min. The reaction vessel is repeatedly rinsed with hydrogen. The corresponding amount of hydrogen is then added under normal pressure. Following the start of the reaction the consumption of hydrogen is measured over time. The hydrogenation experiment is ended after four times the reaction half life. After sample collection the ee values are determined by GC (XE 60) or HPLC (Chiracel OD-H).

Examples 20 to 28 of catalytic hydrogenations with chiral ligands having the formula (III)

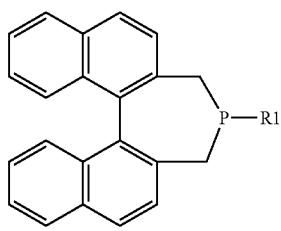

(III)

| Ex. | Ligand R¹ = | Solvent | ee (%) | Config-uration | t/2 (min) | Conversion (%) |
|---|---|---|---|---|---|---|
| 20 | NEt₂ | THF | 88 | R | 1 | 100 |
| 21 | NEt₂ | Toluene | 85 | R | 2 | 100 |
| 22 | NEt₂ | Ethyl acetate | 82 | R | 1 | 100 |
| 23 | t-Bu | THF | 18 | S | 27 | 100 |
| 24 | t-Bu | Toluene | 20 | S | 31 | 100 |
| 25 | t-Bu | Ethyl acetate | 18 | S | 8 | 100 |
| 26 | i-Pr | THF | 46 | R | 1 | 100 |
| 27 | i-Pr | Toluene | 50 | R | 3 | 100 |
| 28 | i-Pr | Ethyl acetate | 36 | R | 2 | 100 |
| 29 | Et | Toluene | 47 | R | 6 | 100 |
| 30 | 4-CH₃OC₆H₄ | Toluene | 74 | R | 12 | 100 |
| 31 | 4-CF₃—C₆H₄ | Toluene | 82 | R | 36 | 100 |
| 32 | 3,5-(CH₃)₂C₆H₃ | Toluene | 67 | R | 17 | 100 |

Alternative work instructions for hydrogenations:

Under an argon atmosphere 0.01 mmol [Rh(COD)₂]BF₄, 0.022 mmol ligand Ju 176/2 (formula (IIIa))

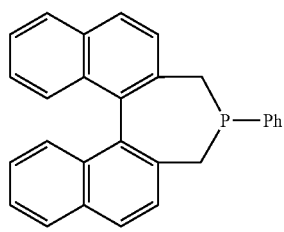

(IIIa)Ligand:Ju 176/2 and 1.0 mmol substrate are added to 15 ml of the dried and degasified solvent in a hydrogenating vessel at a temperature of 25° C. and stirred for 15 min. The reaction vessel is repeatedly rinsed with hydrogen. The corresponding amount of hydrogen is then added under normal pressure. Following the start of the reaction the consumption of hydrogen is measured over time. The hydrogenation experiment is ended after four times the reaction half life. After sample collection the ee values are determined by GC (XE 60) or HPLC (Chiracel OD-H).

Examples 33 to 38 of hydrogenations according to the instructions above.

| Ex. | Sub-strate | Solvent | % ee | Configur-ation | t/2 (min) | Con-version % |
|---|---|---|---|---|---|---|
| 33 | AMe | Toluene | 90 | R | 50 | 100 |
| 34 | AMe | Ethyl acetate | 90 | R | 3 | 100 |
| 35 | AMe | Toluene/SDS | 95 | R | 36 | 100 |
| 36 | AMe | THF | 92 | R | 15 | 100 |
| 37 | AMe | Methanol | 89 | R | 2 | 100 |
| 38 | AMe | Acetone | 88 | R | 3 | 100 |
| 39 | AMe | CH₂Cl₂ | 86 | R | 4 | 100 |
| 36 | aMe | Toluene | 67 | R | 19 | 100 |
| 37 | aMe | Ethyl acetate | 65 | R | 2 | 100 |
| 38 | IMe | Toluene | 39 | S | 300 | 96 |
| 39 | IMe | Ethyl acetate | 78 | S | 7.5 | 100 |

AMe = Z-α-acetamidocinnamic acid methyl ester;
aMe = 2-acetamidoacrylic acid methyl ester
IMe = itaconic acid dimethyl ester Examples 40 to 42: The catalytic hydrogenation is performed as described above, except that the Rh: ligand (IIa) ratio is varied:

| Ex. | Sub-strate | Solvent | Rh:(IIIa) (mmol) | % ee | Configur-ation | T/2 (min) | Conver-sion % |
|---|---|---|---|---|---|---|---|
| 40 | AMe | Ethyl acetate | 0.01:0.01 | 90 | R | 8 | 100 |
| 41 | AMe | Ethyl acetate | 0.01:0.04 | 93 | R | 8 | 100 |
| 42 | AMe | Ethyl acetate | 0.001:0.01 | 92 | R | 77 | 100 |

Examples 43 to 47: Catalytic hydrogenation of other substrates

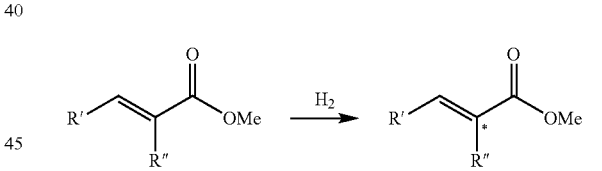

The catalytic hydrogenation is performed as described above, taking into account the details set out in the table below:

| Ex. | Substrate R' | R" | Substrate: Rh:(IIIa) (mmol) | Solvent | % ee | Yield |
|---|---|---|---|---|---|---|
| 43 | 4-CH₃-C₆H₄ | NHAc | 2:0.01:0.02 | Toluene | 90 | 100 |
| 44 | 4-Br-C₆H₄ | NHAc | 2:0.01:0.02 | Toluene | 84 | 100 |
| 45 | 4-NO₂-C₆H₄ | NHAc | 2:0.01:0.02 | Toluene | 90 | 100 |
| 46 | H | CH₂COOMe | 1:0.01:0.02 | Ethyl acetate | 78 | 100 |

Examples 47 to 58 of catalytic hydrogenations:

The hydrogenation is performed as described above. 0.01 mmol [Rh(COD)₂]BF₄ are used as catalyst pre-complex and 0.022 mmol of the compound having the formula (IIIb) (Ju 180/4/2) as ligand. 1.0 mmol substrate is reacted.

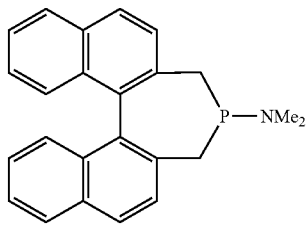

(IIIb)Ju 180/4/2

The results of the hydrogenation are set out in the tables below.

| Ex. | Solvent | Substrate | % ee (batch 1/2/3) | T/2 (min) | Reaction time (h) | Yield in % |
|---|---|---|---|---|---|---|
| 47 | Toluene | Ame | 95/91 (R) | 12/11 | 50/60 | 100/100 |
| 48 | EtOAc | Ame | 92/92 (R) | 1.5/1.5 | 10/10 | 100/100 |
| 49 | THF | Ame | 90/90 (R) | 1/1 | 10/10 | 100/100 |
| 50 | Toluene + SDS | Ame | 93/96 (R) | 7.5/10 | 17/45 | 100/100 |
| 51 | Toluene | Ame | 24/15 (R) | —/— | 20/16 | 20/24 |
| 52 | EtOAc | Ame | 60/62 (R) | 2/2.5 | 20/20 | 100/100 |
| 53 | THF | AMe | 68/68/71 (R) | 3/2/6 | 15/10/35 | 100/100/100 |
| 54 | Toluene + SDS | AMe | 51/24 (R) | —/— | 27/17 | 11/48 |
| 55 | Toluene | Ime | Racemate/racemate | —/— | 17/17 | 13/8 |
| 56 | EtOAc | Ime | Racemate/racemate | —/— | 23/17 | 7/37 |
| 57 | THF | Ime | 2(R)/racemate | —/— | 67/23 | 39/25 |
| 58 | Toluene + SDS | Ime | Racemate/racemate | —/— | 16/20 | 25/16 |

AMe = Z-α-acetamidocinnamic acid methyl ester
aMe = 2-acetamidoacrylic acid methyl ester
IMe = itaconic acid dimethyl ester

The invention claimed is:

1. A chiral ligand having the formula I

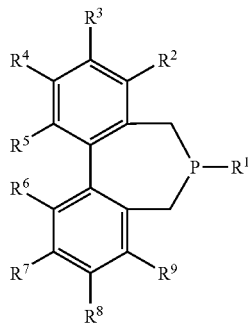

(I)

wherein in formula I $R^1$ represents an ethyl, isopropyl, tert-butyl, $(C_1-C_{12})$-alkylaryl, $(C_1-C_{12})$-alkyl-O-aryl, alkenyl, heteroaromatic aryl, O-alkyl, O-aryl, NH-alkyl, or N-(alkyl)$_2$, wherein the two alkyl radicals can also be linked together directly or via an oxygen bridge, O-(aryl), NH-(aryl), or N-(alkyl)(aryl) radical, $R^2$ to $R^9$ mutually independently have the meaning of $R^1$ or stand for a radical selected from the group consisting of O—CO-alkyl, O—CO-aryl, F, Cl, Br, OH, NO$_2$, Si(alkyl)$_3$, CF$_3$, CN, CO$_2$H, COH, SO$_3$H, CONH$_2$, CONH(alkyl), CON(alkyl)$_2$, SO$_2$(alkyl), SO(alkyl), SO(aryl), SO$_2$(aryl), SO$_3$(alkyl), SO$_3$(aryl), S-alkyl, S-aryl, NH—CO(alkyl), CO$_2$(alkyl), CONH$_2$, CO(alkyl), NHCOH, NHCO$_2$(alkyl), CO(aryl), CO$_2$(aryl), CH═CH—CO$_2$(alkyl), CH═CH—CO$_2$H, PO(aryl)$_2$, PO(alkyl)$_2$, PO$_3$H, PO(O-alkyl)$_2$ and aryl, wherein in each case two or more adjacent radicals can mutually independently also be linked together to form a condensed ring system, and wherein in $R^1$ to $R^9$ alkyl stands for a hydrocarbon radical with 1 to 12 C atoms and alkenyl for a monounsaturated or polyunsaturated hydrocarbon radical with 2 to 4 C atoms, each of which can be linear or branched and can be substituted with Cl, F, alkyl $(C_1-C_{12})$, O-alkyl $(C_1-C_{12})$, $(C_5-C_{10})$ aryl, O—$(C_5-C_{10})$ aryl, NH$_2$, NH(alkyl $(C_1-C_{12})$), N(alkyl $(C_1-C_{12}))_2$, and aryl stands for a five- to ten-membered aromatic radical, which can be substituted with Cl, F, Br, alkyl $(C_1-C_{12})$, O-alkyl $(C_1-C_{12})$, $(C_5-C_{10})$ aryl, O—$(C_5-C_{10})$ aryl, NH$_2$, NH(alkyl $(C_1-C_{12})$), N(alkyl $(C_1-C_{12}))_2$, wherein one to four carbon atoms in the aromatic radical can also be replaced by heteroatoms selected from the group consisting of nitrogen, oxygen and sulfur to form a five- to ten-membered heteroaromatic aryl radical.

2. The chiral ligand according to claim 1, wherein $R^1$ represents a radical selected from the group consisting of an O-alkyl radical and an O-(aryl) radical.

3. The chiral ligand according to claim 1, wherein $R^1$ represents a radical selected from the group consisting of an NH-alkyl radical and an N-(alkyl)$_2$ radical; and wherein the two alkyl radicals can also be linked together directly or via an oxygen bridge, NH-(aryl), or N-(alkyl)(aryl) radicals.

4. The chiral ligand according to claim 1, wherein $R^2$ to $R^9$ mutually independently represent radicals selected from the group consisting of O—CO-alkyl, O—CO-aryl, Br, CONH$_2$, CONH(alkyl), CON(alkyl)$_2$, SO(alkyl), SO(aryl), SO$_2$(alkyl), SO$_2$(aryl), SO$_3$(alkyl), SO$_3$(aryl), NH—CO (alkyl), CO$_2$(alkyl), CONH$_2$, CO(alkyl), NHCOH, NHCO$_2$ (alkyl), CO$_2$(aryl), PO(alkyl)$_2$, PO(O-alkyl)$_2$, hydrogen, alkyl, aryl or heteroaryl, O-alkyl, NH-alkyl, N-(alkyl)$_2$, O-(aryl), NH-(aryl), N-(alkyl)(aryl), F, Cl, OH, CO$_2$H, SO$_3$H, CO(alkyl), CO(aryl), PO(aryl)$_2$, and PO$_3$H.

5. The chiral ligand according to claim 1, wherein $R^1$ to $R^9$ for one or more of these radicals alkyl and alkenyl stand for a hydrocarbon radical with 1 to 4 C atoms, the alkenyl group possessing a double bond, and aryl for a five- to seven-membered aromatic radical.

6. The chiral ligand according to claim 1, wherein heteroaromatic aryl radicals in $R^2$ to $R^9$ comprise one or two nitrogen atoms, one nitrogen and one oxygen atom or one sulfur or one oxygen atom.

7. The chiral ligand according to claim 1, wherein two or more adjacent radicals $R^2$ to $R^9$ are linked together.

8. The chiral ligand according to claim 7, wherein two adjacent radicals $R^2$ to $R^9$ are linked together in such a way that a five- to seven-membered saturated or unsaturated cycloaliphatic ring or a six-membered aromatic ring is formed.

9. The chiral ligand according to claim 1, wherein $R^1$ represents an ethyl, isopropyl, tert-butyl, $(C_1-C_{12})$-alkylaryl, $(C_1-C_{12})$-alkyl-O-aryl, alkenyl, heretoaromatic aryl, O-aryl, O-alkyl, NH-alkyl, N-(alkyl)$_2$, O-(aryl), NH-(aryl), or N-(alkyl)(aryl) radical, $R^2$ to $R^9$ mutually independently have the meaning of $R^1$, hydrogen, F, Cl, OH, $CO_2H$, $SO_3H$, CO(alkyl), CO(aryl), PO(aryl)$_2$, $PO_3H$, wherein in each case two or more adjacent radicals can mutually independently also be linked together to form a condensed ring system, wherein the alkenyl, aryl and heteroaromatic aryl groups are as defined.

10. A catalyst obtained by reacting a metal salt or a metal pre-complex with the chiral ligand according to claim 1.

11. The catalyst according to claim 10, wherein the catalyst comprises a metal selected from the group consisting of palladium, platinum, rhodium, ruthenium, osmium, iridium, cobalt, nickel, and copper.

12. A process for the production of chiral ligands according to claim 1, wherein enantiopure dimethyl compounds having the formula II

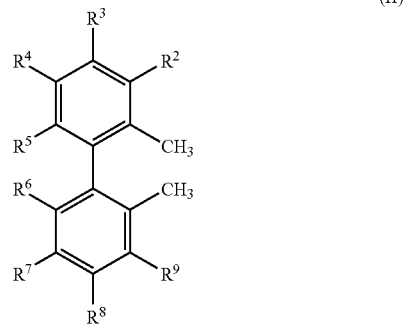

(II)

are lithiated with alkyl lithium compounds and then reacted with aminophosphorus dichlorides, alkyl or aryl phosphorus dichlorides.

13. The process according to claim 12, wherein the radical $R^1$ is subsequently exchanged, wherein a 4-aminophosphepine is converted to 4-chlorophosphepine by HCl/Et$_2$N exchange and then a new radical $R^1$ is introduced by reaction with an amine or an alcohol and a Grignard reagent.

14. A process, comprising:
mixing the chiral ligand as claimed in claim 1 with a metal in a medium and
adding a prochiral or chiral substrate to the medium.

15. A process, comprising:
adding the catalyst as claimed in claim 10 to a medium and
adding a prochiral or chiral substrate to the medium.

16. The process, as claimed in claim 14, wherein said process is selected from the group consisting of hydrosilylation, amination, allyl substitution, Grignard coupling, Heck and Suzuki reaction, hydrocyanation, hydrovinylation, hydroformylation, hydroacylation, and hydrocarboxylation.

17. The process, as claimed in claim 15, wherein said process is selected from the group consisting of hydrosilylation, amination, allyl substitution, Grignard coupling, Heck and Suzuki reaction, hydrocyanation, hydrovinylation, hydroformylation, hydroacylation, and hydrocarboxylation.

18. A process, which comprises:
mixing the chiral ligand as claimed in claim 1 with a metal in a medium;
adding a prochiral or chiral substrate to the medium; and
exposing said medium to hydrogen gas.

19. A process, comprising:
adding the catalyst as claimed in claim 10 to a medium;
adding a prochiral or chiral substrate to the medium; and
exposing said medium to hydrogen gas.

20. The process according to claim 14, which further comprises adding SDS to the medium.

21. The process according to claim 16, which further comprises adding SDS to the medium.

22. The process according to claim 18, which further comprises adding SDS to the medium.

23. The process according to claim 18, which further comprises adding SDS to the medium.

24. The process according to claim 19, which further comprises adding SDS to the medium.

* * * * *